(12) United States Patent
Rogers et al.

(10) Patent No.: US 10,959,673 B1
(45) Date of Patent: Mar. 30, 2021

(54) PRESSURE MANAGEMENT METHODS FOR DETERMINING NON-INCLUSIVE FORCES AND APPARATUSES INCORPORATING THE SAME

(71) Applicant: Toyota Motor Engineering & Manufacturing North America, Inc., Plano, TX (US)

(72) Inventors: Caleb Rogers, Lexington, KY (US); Tyler Flood, Stamping Ground, KY (US)

(73) Assignee: TOYOTA MOTOR ENGINEERING & MANUFACTURING NORTH AMERICA, INC, Plano, TX (US)

( * ) Notice: Subject to any disclaimer, the term of this patent is extended or adjusted under 35 U.S.C. 154(b) by 0 days.

(21) Appl. No.: 15/931,215

(22) Filed: May 13, 2020

Related U.S. Application Data

(63) Continuation of application No. 16/721,212, filed on Dec. 19, 2019.

(51) Int. Cl.
*A61B 5/00* (2006.01)
*G01L 5/22* (2006.01)
*G06F 3/01* (2006.01)

(52) U.S. Cl.
CPC ............ *A61B 5/6806* (2013.01); *G01L 5/228* (2013.01); *G06F 3/014* (2013.01)

(58) Field of Classification Search
CPC ........ A61B 5/6806; G01L 5/228; G06F 3/014
USPC .................................................. 73/862.381
See application file for complete search history.

(56) References Cited

U.S. PATENT DOCUMENTS

| | | | |
|---|---|---|---|
| 6,580,269 B2 | 6/2003 | Hiligsmann et al. | |
| 9,345,424 B2 | 5/2016 | Wang et al. | |
| 9,562,818 B1 * | 2/2017 | Adamski .............. | A61B 5/6843 |
| 9,754,512 B2 | 9/2017 | Kotranza et al. | |
| 2012/0306811 A1 | 12/2012 | Farmer et al. | |
| 2014/0214353 A1 * | 7/2014 | Barfield ................. | G01D 3/036 |
| | | | 702/104 |
| 2016/0041610 A1 * | 2/2016 | Grau ....................... | G01L 5/228 |
| | | | 73/862.381 |
| 2016/0291762 A1 * | 10/2016 | Kim ...................... | G06F 3/0416 |
| 2018/0263563 A1 | 9/2018 | McMillen et al. | |

FOREIGN PATENT DOCUMENTS

JP 4093988 B2 6/2008

OTHER PUBLICATIONS

A novel dataglove calibration method (https://ieeexplore.ieee.org/documenl/5593803) Published: Sep. 30, 2010.

(Continued)

*Primary Examiner* — Octavia Hollington
(74) *Attorney, Agent, or Firm* — Dinsmore & Shohl LLP

(57) ABSTRACT

A method includes determining that a portion of a force applied to a sensor system was applied to a non-inclusive region of the sensor system. An activation area of the non-inclusive region may be determined. A force distribution of the non-inclusive region may be determined. A corresponding force measurement of the non-inclusive region based on the activation area and the force distribution may be calculated.

18 Claims, 9 Drawing Sheets

(56) References Cited

OTHER PUBLICATIONS

IGS cobra glove (https://est-kl.com/manufacturer/synertial/igs-cobra-glove.hlml) Accessed: Jan. 30, 2019.
The artificial skin that allows robots to feel (https://www.cnn.com/2019/11/28/business/robot-artificial-skin-scn/index.html) Published: Nov. 28, 2019.

* cited by examiner

PRESSURE MANAGEMENT METHODS FOR DETERMINING NON-INCLUSIVE FORCES AND APPARATUSES INCORPORATING THE SAME

CROSS-REFERENCE TO RELATED APPLICATION

This application is a continuation application and claims priority to co-pending U.S. patent application Ser. No. 16/721,212, filed Dec. 19, 2019, for "Pressure Management Methods For Determining Non-Inclusive Forces And Apparatuses Incorporating The Same," which is hereby incorporated by reference in its entirety including the drawings.

TECHNICAL FIELD

The present specification generally relates to sensor systems and processes for detecting and measuring a pressure applied to a sensor, and more specifically, to methods for detecting a pressure distribution and localization of non-inclusive forces applied to a sensor system to determine a resultant force.

BACKGROUND

Sensors may be utilized to collect pressure measurements applied thereto. For instance, gloves incorporating sensor technology may be utilized to collect representative pressure measurements experienced along an operator's hand when a force is received thereon. To improve an accuracy of the pressure measurements detected by a sensor, relative parameters that are directly proportionate to a force received along the sensor may be determined and incorporated when computing a resultant force. In instances where a physical force is received along a non-inclusive region, which does not include a sensor, rather than across a sensor, including parameters such as the complete area of the sensor to compute a resultant force may provide inaccurate pressure measurements than that actually experienced on the glove. Accordingly, a determination of a resultant pressure measurement may include inaccuracies due to the relative parameters of the sensor incorporated into computing a pressure measurement applied to the sensor and the lack of sensors included in the non-inclusive region, where a portion of the force was applied. The potential inaccuracy in measuring the detected pressure may be detrimental to the objective of identifying a magnitude of force received thereon.

Accordingly, a need exists for systems and methods that more accurately measure forces and pressures applied to non-inclusive regions of gloves.

SUMMARY

In one embodiment, a method includes determining that a portion of a force applied to a sensor system was applied to a non-inclusive region of the sensor system. An activation area of the non-inclusive region may be determined. A force distribution of the non-inclusive region may be determined. A corresponding force measurement of the non-inclusive region based on the activation area and the force distribution may be calculated.

In another embodiment, a sensor system may include a sensing area disposed along a surface of the sensor system and a non-inclusive region arranged adjacent to the sensing area, wherein the non-inclusive region does not include a sensor. The sensor system further includes a processor that, when executing computer readable and executable instructions of the sensor system, causes the sensor system to: determine that a portion of a force applied to the sensor system was applied to the non-inclusive region of the sensor system; determine an activation area of the non-inclusive region; determine a force distribution of the non-inclusive region; and calculate a corresponding force measurement of the non-inclusive region based on the activation area and the force distribution.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1A:
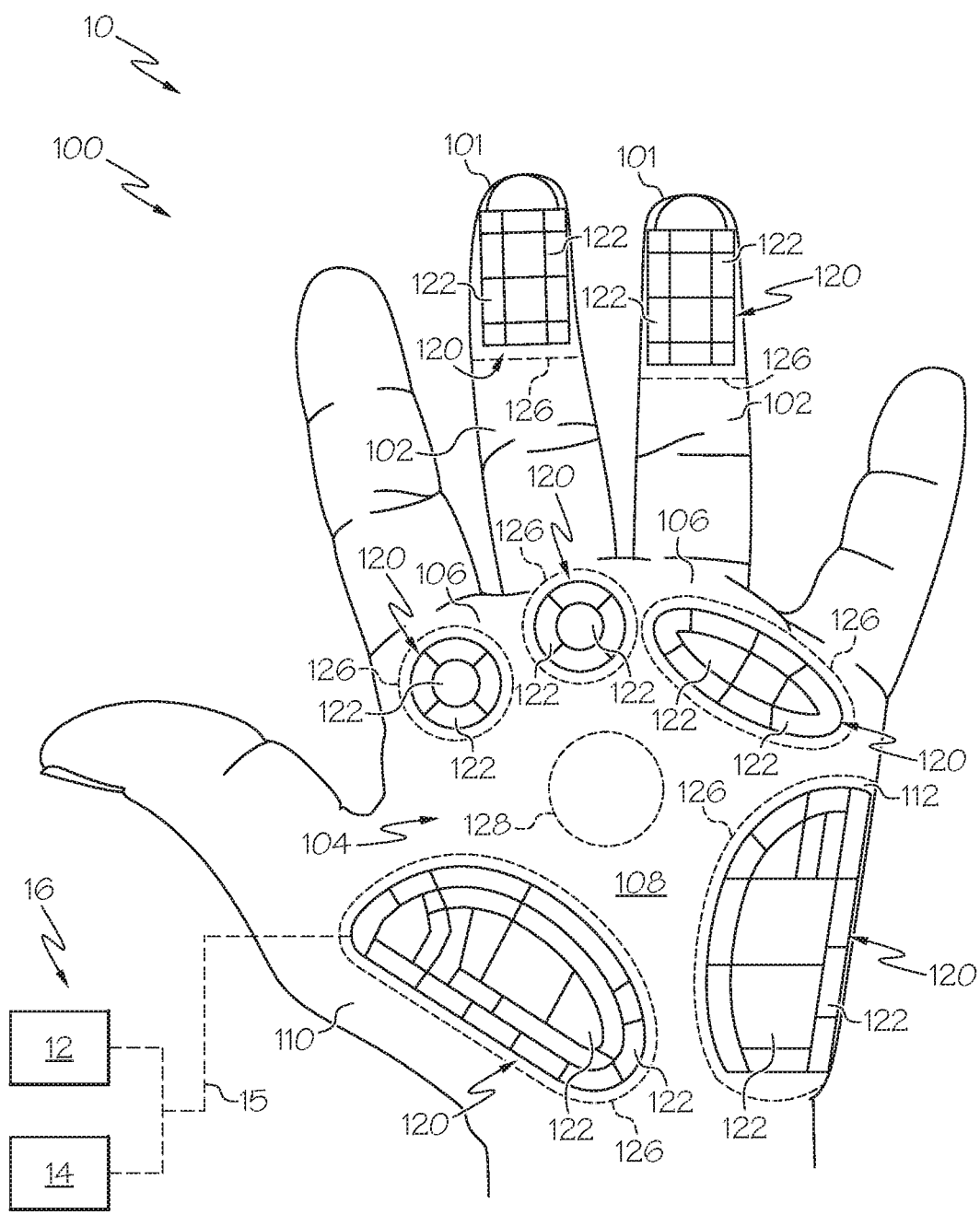
FIG. 1A schematically depicts an illustrative sensing sensor system including a plurality of sensor regions and non-inclusive regions along surfaces of a glove according to one or more embodiments shown and described herein.

Systems may include one or more arrays (e.g., regions) of sensor assemblies positioned thereon designed to collectively detect a force received along the glove. By detecting a physical force applied to the sensor arrays of the glove, an operator of the glove may identify a resultant pressure endured at various locations along the operator's hand. With the pressure data detected by the sensor assemblies of the glove, an operator of the sensor system may adjust a manner in performing a task (e.g., adjusting a physical position, geometry, and/or orientation of an operator's hand) as a result of analyzing said data to minimize the force endured along an operator's hand and thereby reduce instances of possible injury, discomfort, and/or unnecessary-expended labor when performing the task. To determine an appropriate method to perform a task, based on the forces applied to an operator's hand when performing the task, accurately measuring a resultant pressure is desirable. However, in some instances a resultant pressure measurement may vary relative to an actual force received along an operator's hand due to the application of a portion of the force along a non-inclusive region. Inaccuracies of measuring a force may provide challenges in accurately measuring a resultant pressure applied to an operator's hand and in determining an appropriate method in performing a task with the operator's hand.

The present disclosure relates generally to systems and methods that include sensor technology for detecting and measuring forces received along a glove. More specifically, the present disclosure relates to sensor systems and methods that improve an accuracy of measuring a pressure received along a sensor assembly and a non-inclusive region of the glove by determining an actual active area of the non-inclusive region that receives a force thereon for incorporation into actual force computations. Providing a sensor system that localizes a non-inclusive force received adjacent to a sensor may assist in accurately measuring a resultant pressure calculated from a force applied thereto. The sensor system may aid in determining an appropriate method, such as a physical position or orientation, in performing a task by detecting and measuring various forces received at an operator's hand at an actual active area along a surface of the operator's hand with accuracy by localizing the area that the force was received on the sensor system for accurate measurement.

It should be appreciated that the sensor systems and methods disclosed herein may have additional uses. For example, the sensor systems and methods may be used with artificial skin, artificial prosthetic skin, artificial robotic skin, flexible tactile force feedback sensing for robots, smart prosthetics synthetic skin for limbs, anatomical prosthetic tactile force feedback, and artificial intelligence tactile synthetic skin. Specifically, the sensor system may be placed on or within an artificial skin which is used to detect force applied to an area which includes the artificial skin. Additionally, the sensor systems may be arranged on robotic device so that the robotic devices may detect a force applied to the robotic device during an assembly or measuring process.

Referring now to the drawings, FIG. 1A depicts an illustrative network having components for a sensor system 10 according to embodiments shown and described herein. As illustrated in FIG. 1A, the sensor system 10 utilizes a computer network 16 that may include a wide area network (WAN), such as the Internet, a local area network (LAN), a mobile communications network, a public service telephone network (PSTN), a personal area network (PAN), a metropolitan area network (MAN), a virtual private network (VPN), and/or another network. The computer network 16 may generally electronically connect one or more components, systems, and/or devices of the sensor system 10, such as computing devices and/or components thereof. Illustrative systems, components, and/or devices of the sensor system 10 may include, but are not limited to, a computing device 12, a server computing device 14, and a glove apparatus 100.

The computing device 12 is a computing device that provides an interface between an operator of the sensor system 10 and the other components of the sensor system 10 via the computer network 16. The computing device 12 may be used to perform one or more user-facing functions of the sensor system 10, such as allowing a user to analyze data received from another component of the sensor system 10 (e.g., the glove apparatus 100) or inputting information to be transmitted to other components of the sensor system 10 (e.g., the server computing device 14), as described in greater detail herein. Accordingly, the computing device 12 may include at least a display and/or input hardware for facilitating the one or more user-interfacing functions. The computing device 12 may also be used to input additional data into the sensor system 10 that supplements the data stored and received from the glove apparatus 100. For example, the computing device 12 may contain software programming or the like that allows a user to view force data detected by a plurality of sensing regions 122 positioned on the glove apparatus 100, review a load distribution determined by the server computing device 14, and provide supplemental information accordingly, such as calibration values for the plurality of sensing regions 122, as described in greater detail herein.

Still referring to FIG. 1A, the server computing device 14 is a remote server that may receive data from one or more sensing regions 122 of the glove apparatus 100, analyze the received data, generate data (e.g., an estimated localized subarea, load distribution, pressure magnitudes, confidences factors of computed pressure magnitudes, etc.), store data, index data, search data, and/or provide data to the computing device 12 (or components thereof) via the computer network 16. More specifically, the server computing device 14 may employ one or more load distribution and pressure gradient estimation algorithms for the purposes of analyzing data that is received from the glove apparatus 100, as described in greater detail herein. In some embodiments, the server computing device 14 includes one or more hardware components integrated therein and used with the sensor system 10, such as, for example, a non-transitory computer-readable medium for completing the various processes described herein, embodied as hardware, software, and/or firmware, according to embodiments shown and described herein.

The server computing device 14 may further include a processing device, such as a computer processing unit (CPU) that is a central processing unit of the sensor system 10, performing calculations and logic operations to execute a program. The processing device of the server computing device 14, alone or in conjunction with the other components, may include any processing component configured to receive and execute instructions, such as from the glove apparatus 100 and/or the computing device 12. The non-transitory memory medium of the server computing device 14 may include one or more programming instructions thereon that, when executed by a processing device of the server computing device 14, cause the processing device to complete various processes, such as certain processes described herein with respect to analyzing and determining pressure magnitude data upon detecting a force applied to the glove apparatus 100. The programming instructions stored on the non-transitory memory medium of the server computing device 14 may be embodied as a plurality of software logic modules, where each logic module provides programming instructions for completing one or more tasks. As described in greater detail herein, the server computing device 14 is configured to compute a raw confidence and an interpolated confidence factor based on an estimated error probability of a pressure magnitude determined for each of the sensing regions 122 that receive a force thereon. The confidence factor is an evaluation of error in computing the pressure magnitude based on a load distribution and a localized subarea.

Still referring to FIG. 1A, it should be understood that while the computing device 12 is depicted as a personal computer and the server computing device 14 is depicted as a server, these are non-limiting examples. In some embodiments, any type of computing device (e.g., mobile computing device, computer, server, cloud-based network of devices, etc.) may be used for any of these components. Additionally, while each of these computing devices is illustrated in FIG. 1A as a single and separate piece of hardware, this is also merely an example. Each of the computing device 12 and the server computing device 14 may represent a plurality of computers, servers, databases, components, and/or the like. In other embodiments, the computing device 12 and the server computing device 14 may be integrated into a single apparatus such that the sensor system 10 includes fewer components communicatively coupled to one another through the computer network 16. In embodiments where the server computing device 14 is a separate apparatus from that of the computing device 12, the methods described herein provide a mechanism for improving the functionality of the server computing device 14 by moving certain processor-intensive tasks away from the computing device 12 to be completed by an external device that is more adapted for such tasks (e.g., the server computing device 14).

The glove apparatus 100 may generally including at least one finger surface region 102 and a palmar surface region 104. The palmar surface region 104 of the glove apparatus 100 includes a palmar metacarpal region 106, a median palmar region 108, a hypothenar region 110, and a thenar region 112.

The palmar surface region 104 of the glove apparatus 100 includes one or more sensing areas 120 and one or more non-inclusive regions 126, 128 positioned thereon, and in particular along one or more of the palmar metacarpal region 106, the median palmar region 108, the hypothenar region 110, and the thenar region 112. In the present example, the palmar surface region 104 includes three sensing areas 120 and three non-inclusive regions 126 positioned along the palmar metacarpal region 106, one sensing area 120 and one non-inclusive region 126 positioned along the hypothenar region 110, and one sensing area 120 and one non-inclusive region 126 positioned along the thenar region 112. The one or more sensing areas 120 may be secured to and attached to the glove apparatus 100 by various methods, including, but not limited to, printing the one or more sensing areas 120 onto a fabric of the glove apparatus 100, weaving the one or more sensing areas 120 into a fabric of the glove apparatus 100, adhesively securing the one or more sensing areas 120 to the glove, and/or the like. The non-inclusive regions 126 may be arranged adjacent to a corresponding sensing area 120, or may be arranged on any portion of the surface of the sensor system 10 where a sensing area 120 is not arranged, such as non-inclusive region 128. It should be understood that additional and/or fewer sensing areas 120 and non-inclusive regions 126, 128 may be positioned along various anatomical regions of the palmar surface region 104 than those shown and depicted herein without departing from the scope of the present disclosure.

Still referring to FIG. 1A, the one or more sensing areas 120 of the glove apparatus 100 include a plurality of sensing regions 122 positioned therein. In some embodiments, the plurality of sensing regions 122 of each of the one or more sensing areas 120 are sized, shaped and positioned along the palmar surface region 104 relative to an intended-task to be performed with the glove apparatus 100. In other words, a location and profile of the one or more sensing areas 120, and the plurality of sensing regions 122 included therein, along the palmar surface region 104 of the glove apparatus 100 may be determined based on a predetermined use of the glove apparatus 100. Accordingly, the one or more sensing areas 120 and non-inclusive regions 126 are sized and positioned along the corresponding regions 106, 108, 110, 112 of the palmar surface region 104 that generally receive a force load thereon when performing the predetermined task with an operator's hand. As will be described in greater detail herein, the one or more sensing areas 120 and non-inclusive regions 126 may be positioned along the finger surface region 102 of the glove apparatus 100 for instances where an operator's hand generally receives a force load thereon when performing a predetermined task. In addition to the one or more sensing areas 120 and non-inclusive regions 126 being positioned along the glove apparatus 100 at locations where a static, push load may be received during performance of a predetermined task, the one or more sensing areas 120 and non-inclusive regions 126 may be further positioned along portions of the glove apparatus 100, and in particular the palmar surface region 104, where transverse, slidable loads may be received that generate indirect forces along an operator's hand.

The plurality of sensing regions 122 of each of the one or more sensing areas 120 are further sized, shaped and positioned along the palmar surface region 104 relative to a surface curvature of an operator's hand. In other words, a profile of the one or more sensing areas 120, the plurality of sensing regions 122 included therein, and the one or more non-inclusive regions 126, 128, along the palmar surface region 104 of the glove apparatus 100 may be determined based on a surface curvature of an operator's hand along the particular region 106, 108, 110, 112 of the palmar surface region 104 where the sensing area 120 is located. In the present example, the plurality of sensing regions 122 of the sensing areas 120 and the non-inclusive region 126 located along the palmar metacarpal region 106 are sized and shaped relative to the curvature and size of the palmar metacarpal region 106. Accordingly, the plurality of sensing regions 122 of the sensing areas 120 located along the palmar metacarpal region 106 are relatively small and circular due to a corresponding contour of the palmar metacarpal region 106.

Still referring to FIG. 1A, the plurality of sensing regions 122 of the sensing areas 120 and the non-inclusive regions 126 located along the hypothenar region 110 and the thenar region 112 are sized and shaped relative to the curvature and size of the hypothenar region 110 and the thenar region 112, respectively. Accordingly, the plurality of sensing regions 122 of the sensing areas 120 and the non-inclusive regions 126 located along the hypothenar region 110 and the thenar region 112 are relatively large and elongated due to a corresponding contour of the hypothenar region 110 and the thenar region 112. It should be understood that the plurality of sensing regions 122 within an individual sensing area 120 may vary in size and geometry relative one another. It should further be understood that various other sizes, geometries and positions of the one or more sensing areas 120 and non-inclusive regions 126, 128, and in particular the sensing regions 122 positioned therein, along the palmar surface region 104 may be included on the glove apparatus 100 than those shown and depicted herein. As will be described in greater detail herein, with the glove apparatus 100 including a plurality of sensing regions 122 within the one or more sensing areas 120 and non-inclusive regions 126, the glove apparatus 100 is configured to sense force loads applied thereto along general, non-discrete anatomical portions of an operator's hand (i.e., along the sensing regions 122). It should be understood that with the inclusion of the plurality of sensing regions 122 within the one or more sensing areas 120, the glove apparatus 100 may provide a general indication of a location along the glove apparatus 100 where a pressure is received. As will be described in greater detail herein, inclusion of individual, discrete sensors may provide a specific indication of the location in which the sensor system receives a pressure.

Figure 1B:
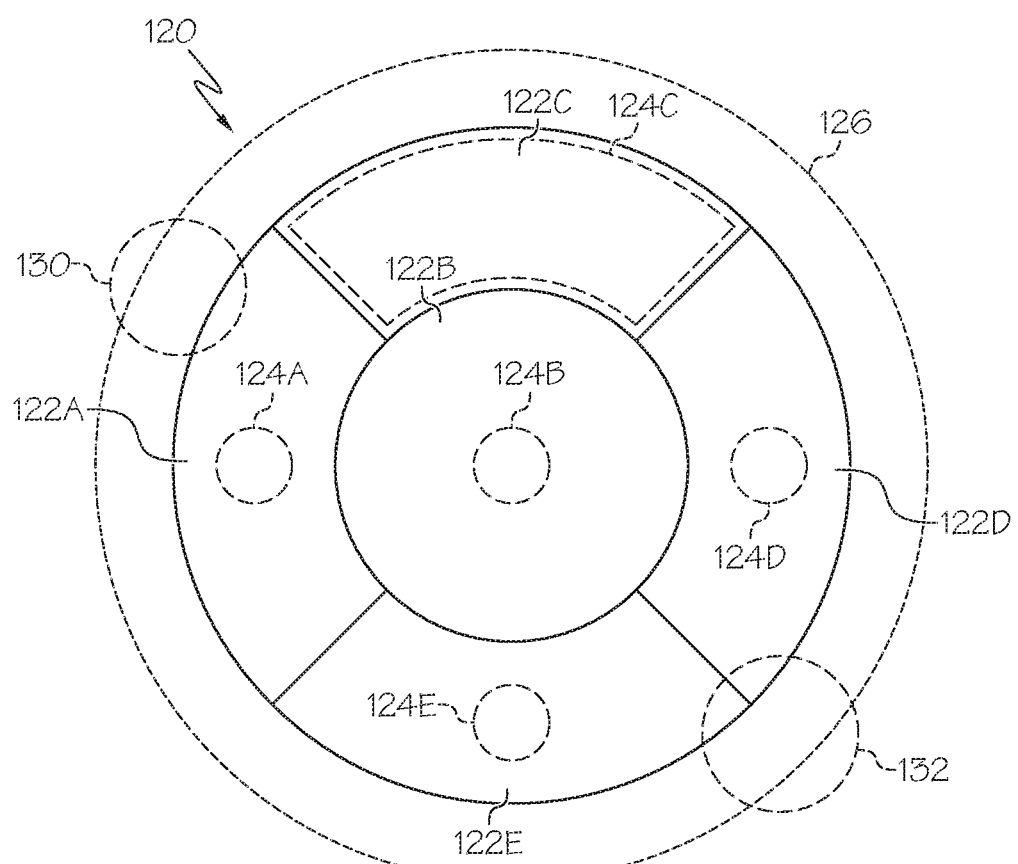
FIG. 1B schematically depicts a sensing area and a non-inclusive region of the illustrative sensing sensor system of FIG. 1A according to one or more embodiments shown and described herein.
Figure 1C:
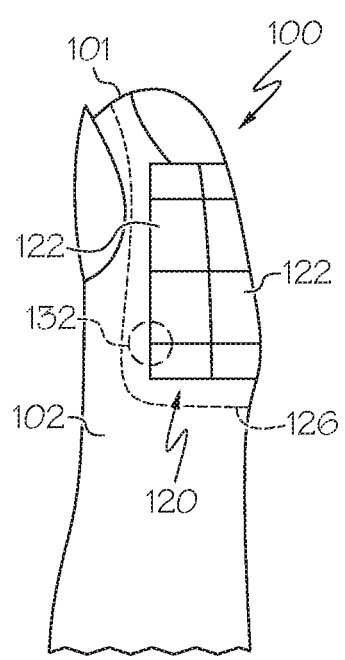
FIG. 1C schematically depicts a sensing area and a non-inclusive region of the illustrative sensing sensor system of FIG. 1A according to one or more embodiments shown and described herein.

Referring now to FIGS. 1A, 1B, and 1C, the glove apparatus 100 may further include one or more sensing areas 120 and non-inclusive regions positioned along one or more finger surface regions 102. The one or more sensing areas 120 include a plurality of sensing regions 122 positioned therein that are relatively sized and shaped in correspondence to a predetermined use of the glove apparatus 100 and/or a surface curvature of the finger surface region 102. For example, the plurality of sensing regions 122 of the sensing area 120 may extend up to and wrap around a distal end 101 of the finger surface region 102 when the distal end 101 generally receives force loads thereon when performing a predetermined task with an operator's hand. A non-inclusive region 126 may be arranged adjacent to the sensing area 120. Additionally or alternatively, by way of further example, the plurality of sensing regions 122 of the sensing area 120 may be curved along the finger surface region 102 in correspondence to a surface contour of an operator's hand at the finger surface region 102, as depicted in FIG. 1C. Although a single sensing area 120 is shown and described on the finger surface region 102 of the present example, it should be understood that additional and/or fewer sensing areas 120 and non-inclusive regions 126 may be positioned along various other anatomical portions of the finger surface region 102 without departing from the scope of the present disclosure. Further, it should be understood that the plurality of sensing regions 122 within an individual sensing area 120 may vary in size and shape relative one another and various other sizes, shapes and positions of the one or more sensing areas 120 and sensing regions 122 along the finger surface region 102 may be included on the glove apparatus 100 than those shown and depicted herein.

Still referring to FIG. 1A, in the present example the plurality of sensing regions 122 extend along curved anatomical portions of the finger surface region 102, in addition to planar anatomical portions, to thereby position at least one sensing region 122 of the sensing area 120 along each anatomical portion of the finger surface region 102 that generally receives a force load. The plurality of sensing regions 122 of the sensing area 120 positioned along the curved portions of the finger surface region 102 are form-fitted to the curvature of the anatomical shape of an operator's finger. Although a single sensing area 120 is shown and described on the finger surface region 102 of the present example, it should be understood that additional and/or fewer sensing areas 120 may be positioned along various other anatomical portions of the finger surface region 102 without departing from the scope of the present disclosure. Further, it should be understood that the plurality of sensing regions 122 within an individual sensing area 120 and/or plurality of sensors 124 within an individual sensing region 122 may vary in size and shape relative one another and various other sizes, shapes and positions of the one or more sensing areas 120 and sensing regions 122 along the finger surface region 102 may be included on the glove apparatus 100 than those shown and depicted herein.

Referring now to FIG. 1B, an example sensing area 120 and a non-inclusive region 126 for FIG. 1A is depicted. Each sensing area 120 may include a plurality of various and different sensing regions 122, such as a first sensing region 122A including a first sensor 124A, a second sensing region 122B including a second sensor 124B, a third sensing region 122C including a third sensor 124C, a fourth sensing region 122D including a fourth sensor 124D, and a fifth sensing region 122E including a fifth sensor 124E. The sensors 124A-124E may be arranged underneath each sensing region so that a force applied to any portion of the sensing regions 122A-122E will apply a force to the sensor. The sensing regions 122A-122E may be adjacent to one another, or have a gap provided between each sensing region. Additionally, the sensing regions 122A-122E may be arranged in any configuration in order to accurately detect an applied force, including adding additional sensing regions to the sensing area 120. In embodiments, the sensor 124C may be shaped to correspond to the shape of the sensing region 122C to ensure any force applied to the sensing region 122C is detected by the sensor 124C. It should be appreciated that any of the sensors 124A-124E may be shaped to correspond to their respective sensing regions 122A-122E. The non-inclusive region 126 substantially encompasses the sensing area 120 since the sensing regions 122A-122E are arranged adjacent to one another. In embodiments, if a sensing area 120 included sensing regions 122 which were not arranged adjacent to one another, but included gaps between the sensing regions 122, than a non-inclusive region 126 would be arranged within the gap between sensing regions 122. As depicted, a force 130 may be applied to the sensing region 122A, and detected by the sensor 124A. However, the force 130 is not fully applied to the sensing region 122A, with a portion of the force 130 being applied to the non-inclusive region 126. Therefore, the total applied force is not being detected by the sensor 124A. Additionally, the force 132 may be applied to a portion of the sensing region 122D and the sensing region 122E, where the force 132 is detected by sensors 124D and 124E. Similarly, a portion of the force 132 is applied to the non-inclusive region 126. Therefore, the total applied force is not being detected by the sensors 124D and 124E. An example of force 130 and force 132 would be the circular profile of a bolt being pressed upon for insertion.

A material composition of the one or more sensing areas 120 along the finger surface region 102 may vary relative to the one or more sensing areas 120 positioned along the palmar surface region 104 to retain adequate finger tactility for the glove apparatus 100 along the finger surface regions 102. In particular, materials providing a reduced rigidity for the sensing areas 120 along the finger surface regions 102 to thereby preserve ease of movement of the finger surface regions 102 by an operator of the glove apparatus 100. Additionally, a material thickness of the one or more sensing areas 120 along the finger surface region 102 may vary relative to the one or more sensing areas 120 positioned along the palmar surface region 104 to provide sufficient maneuverability for the glove apparatus 100 along the finger surface regions 102.

Figure 2A:
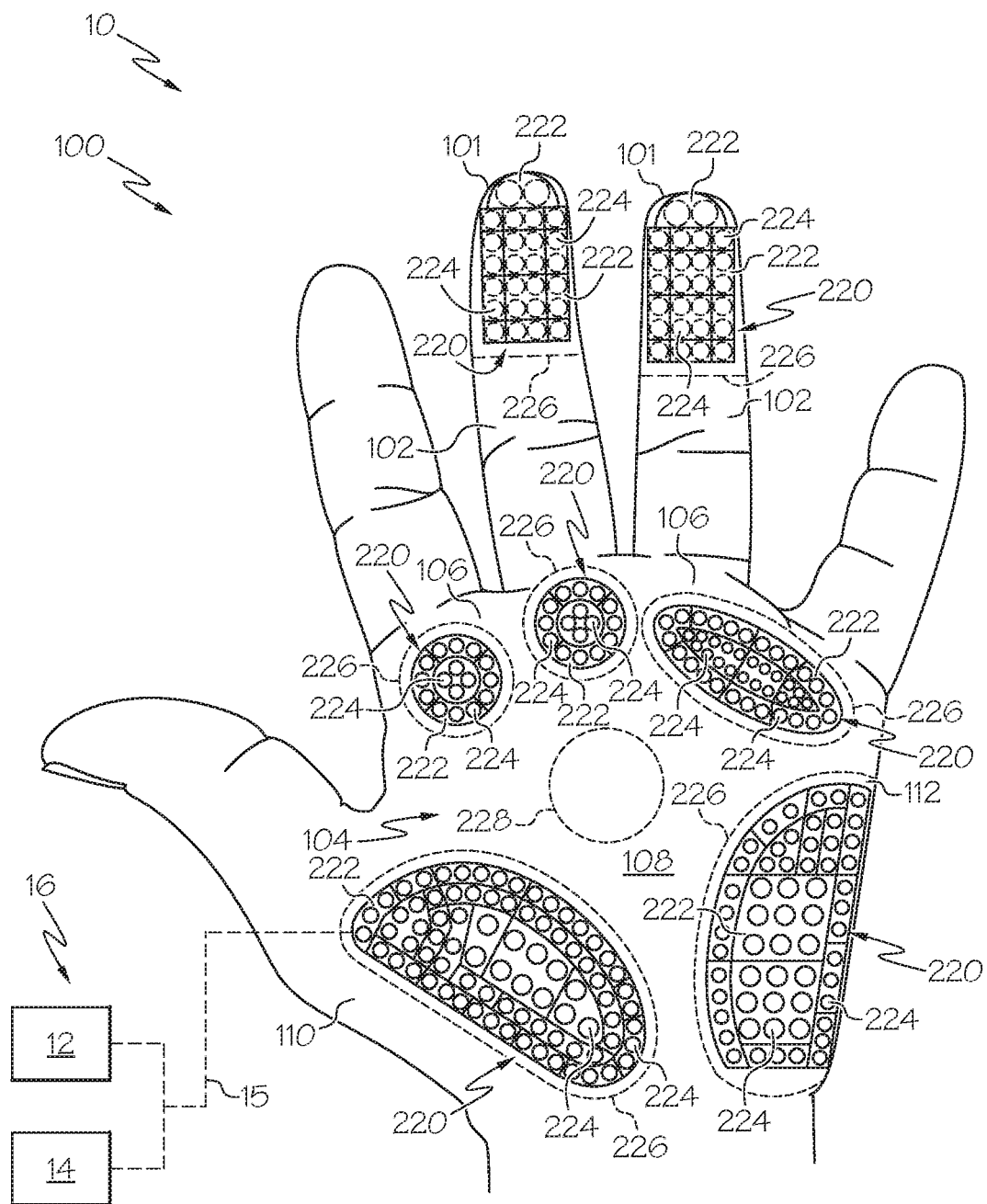
FIG. 2A schematically depicts another illustrative sensing sensor system including a plurality of sensors and non-inclusive regions along surfaces of a glove according to one or more embodiments shown and described herein.

Referring now to FIG. 2A, a sensor system 20 is depicted including another illustrative glove apparatus 200. Except as otherwise described below, it should be understood that the glove apparatus 200 is substantially similar to the glove apparatus 100 described above such that like reference numerals are used to identify like components. However, the glove apparatus 200 is different than the glove apparatus 100 in that the glove apparatus 200 includes one or more sensing areas 220 having at least one sensing region 222 disposed therein, with each sensing region 222 including a one or more sensors 224. In the present example, the palmar surface region 104 includes three sensing areas 220 and one or more non-inclusive regions 226, 228 positioned along the palmar metacarpal region 106, one sensing area 220 and one or more non-inclusive regions 226, 228 positioned along the hypothenar region 110 and one sensing area 220 and one or more non-inclusive regions 226, 228 positioned along the thenar region 112. Each of the sensing areas 220 of the glove apparatus 200 include at least one sensing region 222 and one or more non-inclusive regions 226, 228, and in some instances two or more sensing regions 222, with each of the sensing regions 222 including at least one individual, discrete sensor 224 positioned therein. In some embodiments, the sensing areas 220 include a plurality of sensing regions 222 and the each of the plurality of sensing regions 222 include a plurality of sensors 224. The one or more sensing areas 220 and one or more non-inclusive regions 226, 228 may be secured to and attached to the glove apparatus 200 by various methods, including, but not limited to, printing the one or more sensing areas 220 onto a fabric of the glove apparatus 200, weaving the one or more sensing areas 220 into a fabric of the glove apparatus 200, adhesively securing the one or more sensing areas 220 to the glove, and/or the like. It should be understood that additional and/or fewer sensing areas 220 and/or sensors 224 may be positioned along various anatomical regions of the palmar surface region 104 than those shown and depicted herein without departing from the scope of the present disclosure.

In some embodiments, the plurality of sensors 224 of each of the one or more sensing areas 220 are sized, shaped and positioned along the palmar surface region 104 relative to an intended-task to be performed with the glove apparatus 200. In other words, a location and profile of the one or more sensing areas 220, and the plurality of sensors 224 included therein, along the palmar surface region 104 of the glove apparatus 200 may be determined based on a predetermined use of the glove apparatus 200. Accordingly, the one or more sensing areas 220 and one or more non-inclusive regions 226, 228 are sized and positioned along the corresponding regions 106, 108, 110, 112 of the palmar surface region 104 that generally receive a force load thereon when performing the predetermined task with an operator's hand. As will be described in greater detail herein, the one or more sensing areas 220, and in particular the plurality of sensors 224, may be positioned along the finger surface region 102 of the glove apparatus 200 for instances where an operator's hand generally receives a force load thereon when performing a predetermined task.

Still referring to FIG. 2A, the plurality of sensors 224 of each of the one or more sensing areas 220 are further sized, shaped and positioned along the palmar surface region 104 relative to a surface curvature of an operator's hand. In other words, a profile of the one or more sensing areas 220, and the plurality of sensors 224 included therein, along the palmar surface region 104 of the glove apparatus 200 may be determined based on a surface curvature of an operator's hand along the particular region 106, 108, 110, 112 of the palmar surface region 104 where the sensing area 220 is located. In the present example, the plurality of sensors 224 of the sensing areas 220 located along the palmar metacarpal region 106 are sized and shaped relative to the curvature and size of the palmar metacarpal region 106. Accordingly, the plurality of sensors 224 of the sensing areas 220 located along the palmar metacarpal region 106 are relatively small due to a corresponding contour of the palmar metacarpal region 106.

The plurality of sensors 224 of the sensing areas 220 and the non-inclusive regions 226 located along the hypothenar region 110 and the thenar region 112 are sized and shaped relative to the curvature and size of the hypothenar region 110 and the thenar region 112, respectively. Accordingly, the plurality of sensors 224 of the sensing areas 220 and the non-inclusive regions 226 located along the hypothenar region 110 and the thenar region 112 are relatively larger due to a corresponding contour of the hypothenar region 110 and the thenar region 112. It should be understood that the plurality of sensors 224 within an individual sensing area 220 may vary in size and shape relative one another. It should be further understood that various other sizes, shapes and positions of the one or more sensing areas 220, and in particular the sensors 224 positioned therein, along the palmar surface region 104 may be included on the glove apparatus 200 than those shown and depicted herein. As will be described in greater detail herein, with the glove apparatus 200 including a plurality of sensors 224 within the one or more sensing areas 220, the glove apparatus 200 is configured to sense force loads applied thereto along particular, discrete anatomical portions of an operator's hand (i.e., on the sensors 224). It should be understood that with the inclusion of the plurality of individual, discrete sensors 224 within the one or more sensing areas 220, the glove apparatus 200 may provide a specific indication of a location along the glove apparatus 200 where a pressure is received.

Figure 2B:
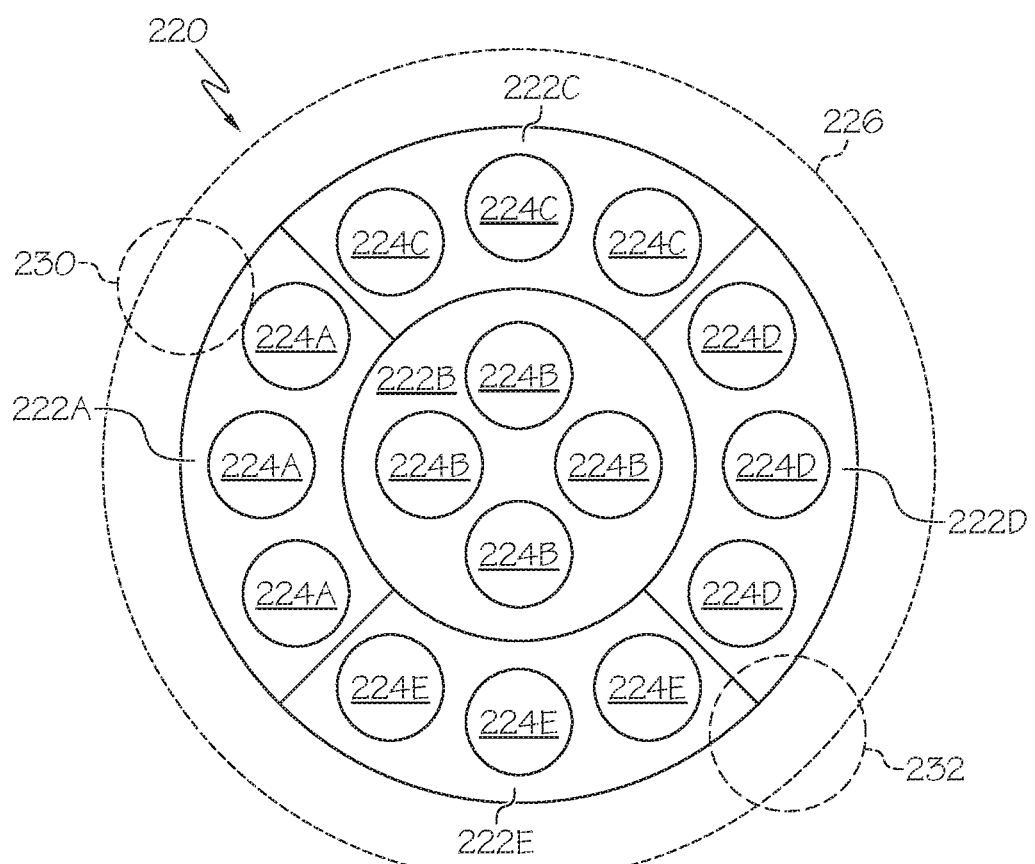
FIG. 2B schematically depicts a sensing area and a non-inclusive region of the illustrative sensing sensor system of FIG. 2A according to one or more embodiments shown and described herein.
Figure 2C:
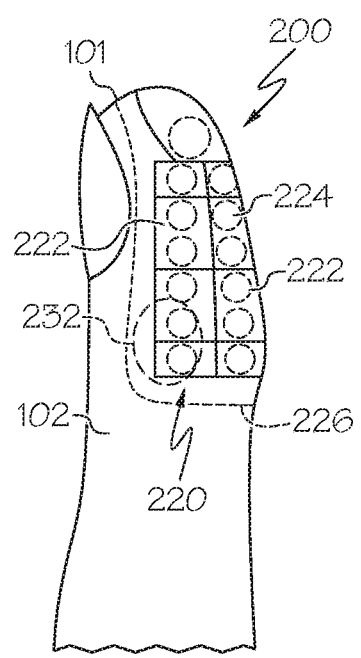
FIG. 2C schematically depicts a sensing area and a non-inclusive region of the illustrative sensing sensor system of FIG. 2A according to one or more embodiments shown and described herein.

Referring now to FIGS. 2A, 2B, and 2C, the glove apparatus 200 may further include one or more sensing areas 220 and one or more non-inclusive regions 226 positioned along one or more finger surface regions 102. The one or more sensing areas 220 include a plurality of sensors 224 positioned therein that are relatively sized and shaped in correspondence to a predetermined use of the glove apparatus 200 and/or a surface curvature of the finger surface region 102. For example, the plurality of sensors 224 of the sensing area 220 may extend up to and wrap around the distal end 101 of the finger surface region 102 when the distal end 101 generally receives force loads thereon when performing a predetermined task with an operator's hand. Additionally or alternatively, by way of further example, the plurality of sensors 224 of the sensing area 220 may be curved along the finger surface region 102 in correspondence to a surface contour of an operator's hand at the finger surface region 102, as depicted in FIG. 2C.

In the present example, the plurality of sensors 224 extend along curved anatomical portions of the finger surface region 102, in addition to planar anatomical portions, to thereby position at least one sensor 224 of the sensing area 220 along each anatomical portion of the finger surface region 102 that generally receives a force load. Although a single sensing area 220 is shown and described on the finger surface region 102 of the present example, it should be understood that additional and/or fewer sensing areas 220 may be positioned along various other anatomical portions of the finger surface region 102 without departing from the scope of the present disclosure. Further, it should be understood that the plurality of sensors 224 within an individual sensing area 220 may vary in size and shape relative one another and various other sizes, shapes and positions of the one or more sensing areas 220 and sensors 224 along the finger surface region 102 may be included on the glove apparatus 200 than those shown and depicted herein.

Referring now to FIG. 2B, an example sensing area 220 and non-inclusive region 226 for FIG. 2A is depicted. Each sensing area 220 may include a plurality of various and different sensing regions 222, such as a first sensing region 222A including a first plurality of sensors 224A, a second sensing region 222B including a second plurality of sensors 224B, a third sensing region 222C including a plurality of sensors 224C, a fourth sensing region 222D including a fourth plurality of sensors 224D, and a fifth sensing region 222E including a fifth plurality of sensors 224E. The plurality of sensors 224A-224E may be arranged underneath each sensing region or above each sensing region so that a force applied to any portion of the sensing regions 222A-222E will apply a force to at least one of the plurality of sensors 224A-224E. The sensing regions 222A-222E may be adjacent to one another, or have a gap provided between each sensing region. Additionally, the sensing regions 222A-222E may be arranged in any configuration in order to accurately detect an applied force, including adding additional sensing regions to the sensing area 220. The non-inclusive region 226 substantially encompasses the sensing area 220 since the sensing regions 222A-222E are arranged adjacent to one another. In embodiments, if a sensing area 220 included sensing regions 222 which were not arranged adjacent to one another, but included gaps between the sensing regions 222, than a non-inclusive region 226 would be arranged within the gap between sensing regions 222. As depicted, a force 230 may be applied to the sensing region 222A, and detected by the plurality of sensors 224A. However, the force 230 is not fully applied to the sensing region 222A, with a portion of the force 230 being applied to the non-inclusive region 226. Therefore, the total applied force is not being detected by the plurality of sensors 224A. Additionally, the force 232 may be applied to a portion of the sensing region 222D and the sensing region 222E, where the force 232 is detected by the plurality of sensors 224D and 224E. Similarly, a portion of the force 232 is applied to the non-inclusive region 226. Therefore, the total applied force is not being detected by the plurality of sensors 224D and 224E. An example of force 230 and force 232 would be the circular profile of a bolt being pressed upon for insertion.

As mentioned above, the various components of the sensor systems 10, 20 described with respect to FIGS. 1A-2B may be used to carry out one or more processes and/or provide functionality for receiving force data from the one or more sensing areas 120, 220 of the glove apparatuses 100, 200, processing the force data, and determining estimated localized subareas of sensing regions 122 and/or sensors 224, load distributions across the sensing regions 122 and/or sensors 224, and/or pressure magnitudes thereon from the processed force data. The various components of the sensor systems 10, 20 may further be used to carry out one or more processes and/or provide functionality for improving an accuracy of the estimated pressure magnitude determination, and in particular, the formula utilized by the server computing device 14 to determine accurate pressure measurements from a force received along the glove apparatuses 100, 200. An illustrative example of the various processes is described with respect to FIGS. 3-4.

Figure 3:
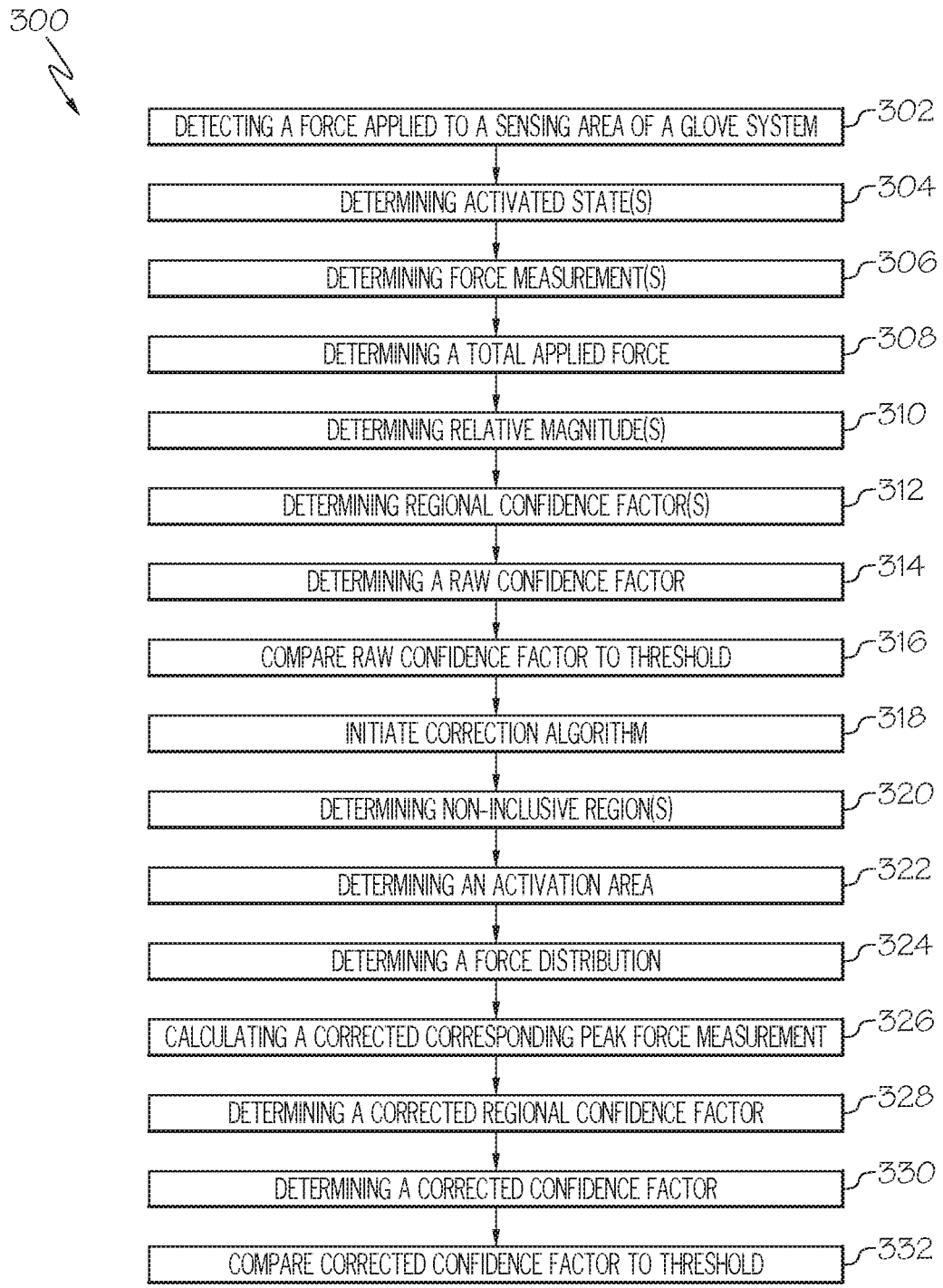
FIG. 3 depicts a flow diagram of an illustrative method of distributing a force across the sensing area and non-inclusive region of the sensing sensor system of FIG. 1B according to one or more embodiments shown and described herein.

Referring now to the flow diagram of FIG. 3 in conjunction with FIGS. 1A and 1B, an illustrative method 300 of localizing and measuring a force load applied to the glove apparatus 100 is schematically depicted. More specifically, the glove apparatus 100 is operable to measure a resultant pressure generated from a force load received along the one or more sensing areas 120 on a surface of an occupant's hand. The depiction of FIG. 3 and the accompanying description below is not meant to limit the subject matter described herein or represent an exact description of how forces may be localized and measured, but instead is meant to provide a simple schematic overview to illustrate the general force localization characteristics of the method described herein.

Referring now to FIG. 3, in conjunction with the sensor system 10 of FIGS. 1A and 1B, a flow diagram is schematically depicted of an illustrative method 300 of determining a pressure magnitude in response to the glove apparatus 100 receiving a force applied thereon. Initially, at step 302, a force applied to a sensing area 120 of a sensor system 10 is detected. Referring to FIG. 1B, the sensing area 120 includes a first sensing region 122A and a second sensing region 122B, the first sensing region 122A including a first sensor 124A, and the second sensing region including a second sensor 124B. As stated above, a sensing area 120 may include a plurality of sensing regions 122A-E, where each sensing region 122A-E includes a sensor 124A-E, as depicted in FIG. 1B. The applied force generates an electrical signal within each sensor 124A-E that has a force applied to a corresponding sensing region 122A-E. This allows the sensors 124A-E arranged within the sensing regions 122A-E to detect the force applied to the sensing regions 122A-E. In this instance, the force data detected by the sensors 124A-E is transmitted to the server computing device 14 of the sensor system 10 via the computer network 16 in the form of an electrical signal 15. As a user wears the glove apparatus 100 and then performs some task (e.g., pushing a box, inserting a screw), a force is applied to the glove apparatus 100. This input force is received by the sensing areas 120 which are arranged on the surface of the glove apparatus 100.

At step 304, activated states of sensors of the plurality of sensing regions are determined. Referring to FIG. 1B, as the force is applied to the sensing area 120, an electrical signal is produced by the sensors 124A-E of the sensing regions 122A-E in response to the force. The electrical signal can be produced through a piezoelectric material, a potentiometer, or the like arranged within the sensing areas 120.

The server computing device 14 determines whether a state of the sensing regions 122A-E receiving the force is in an activated state or an inactivated state. The determination of whether a sensing region 122A-E is in an activated state is made based on the electrical signals of the sensors 124A-E of the sensing regions 122A-E and the electrical signals of the sensors 124A-E of other sensing regions 122A-E. For example, if a single sensing region, for example, the fifth sensing region 122E, including sensor 124E, produces an electrical signal significantly less that the other sensing regions 122A-D, then it would be determined that the fifth sensing region 122E is in an inactivated state, and may be removed from further calculations, while the sensing regions 122A-122D may be determined to be in an activated state. Accordingly, it should be understood that in some instances the sensing regions 122A-E that receive a force applied thereto may not detect the force along the individual, discrete area of the sensing regions 122A-E.

At step 306, force measurements are determined. The determination of the force measurements may be based on the electrical signals of the sensors 124A-E. For example, a first force measurement of the first sensor 124A may be determined based on a generated electrical signal of the first sensor 124A. In some embodiments, the first force measurement of the first sensor 124A is determined based on a peak generated electrical signal of the first sensor 124A. As a movement is performed by a user, the electrical signal of the first sensor 124A is recorded (e.g., for a time interval of 5 seconds). After the movement is performed, that electrical signal is compared to a corresponding calibration curve for the first sensor 124A. The peak force over the time interval experienced by the first sensor 124A is then determined. Additionally, for example, a second force measurement of the second sensor 124B may be determined based on a generated electrical signal of the second sensor 124B. In some embodiments, the second force measurement of the second sensor 124B is determined based on a peak generated electrical signal of the second sensor 124B. Similar to the how the force measurement of the first sensor 124A is determined, as a movement is performed by a user, the electrical signal of the second sensor 124B is recorded (e.g., for a time interval of 5 seconds). After the movement is performed, that electrical signal is compared to a corresponding calibration curve for the second sensor 124B. The peak force over the time interval experienced by the second sensor 124B is then determined. During a procedure, a user may push on an object while wearing the sensor system 10. Over the time interval of the procedure, the force applied is detected at a sampling rate of 20-40 Hz, although other sampling rates may be considered. The peak electrical signals generated by sensing regions 122A-E may be translated into peak force values based on a stored calibration curve. The stored calibration curve may be compiled in a lab setting where various known forces were applied to the sensing regions 122A-E, and the corresponding electrical signals of the sensors 124A-E were recorded in order to create the stored calibration curve over the effect measuring range of the sensing regions 122A-E. For example, if a voltage of 2 volts is being output by the first sensor 124A of the first sensing region 122A, then the corresponding force value when the first sensor 124A is detecting 2 volts may be 10 lbf applied to the first sensing region 122A.

Still referring to FIG. 3, at step 308, a total applied force is determined. Referring to the example being described in the preceding paragraphs, the total applied force may be determined based on the first force measurement and the second force measurement. The total applied force is determined by summing the first force measurement and the second force measurement of the first sensor 124A and the second sensor 124B, respectively. After each sensing region 122A-E has its peak force measurements calculated based on the stored calibration curves, each of the peak force measurements are summed together to determine the peak total applied force across the sampling rate. For example, the total applied force is represented by the following equation: $F_{Total}=F_1+F_2+ \ldots +F_N$, where N is the total number of sensing regions 122A-E within the sensing area 120.

Still referring to FIG. 3, at step 310, relative magnitudes of the sensing regions are determined. Referring to the example described in the preceding paragraphs, a first relative magnitude of the first sensing region 122A is determined based on the first force measurement, a first area of the first sensing region 122A, and at least a portion of the total area of the sensing area 120. Additionally, at step 310, a second relative magnitude of the second sensing region 122B is determined based on the second force measurement, the first area of the first sensing region 122A, and at least a portion of the total area of the sensing area 120. As stated above, a sensing area 120 is broken into various sensing regions 122A-E of different sizes across which a total force is applied. The relative magnitude ($F_R$) of a sensing region 122A-E is represented by the equation: Relative Magnitude ($F_{RN}$)=(Applied Force ($F_N$)/Area of Sensing Region ($A_N$)). Since the total applied force is applied across the sensing area 120, each of the sensing regions 122A-E may be related to one another based on the area of each sensing region 122A-E and the total applied force to the sensing area 120. For example, if the first sensing region 122A has half as much area as a second sensing region 122B, then the force applied to the second sensing region 122B ($F_2$) in terms of the force applied to the first sensing region 122A ($F_1$) would be half of $F_1$. A system equation for each individual sensing region 122A-E within a sensing area 120 may be created, placing the forces applied to each sensing region 122A-E in terms of that particular sensing region's measured peak applied force. If the sensing regions 122A-E of the sensing area 120 all had the applied force applied across their total area, then each of the system equations for the sensing regions 122A-E would equal the total applied force. If a sensing region 122A-E did not have a force applied across its total area, then the force calculated by the system equation using the relative magnitudes would be less than the total applied force.

At step 312, regional confidence factors are determined. Referring to the example described in the preceding paragraphs, a first regional confidence factor for the first sensing region 122A is determined based on the first relative magnitude, and the total applied force. Additionally, for example, a second regional confidence factor for the second sensing region 122B is determined based on the second relative magnitude, and the total applied force. The equation to calculate a regional confidence factor is as follows: Regional Confidence Factor ($RCF_N$)=$F_{RN}/F_{Total}$. If a sensing region 122A-E had the total applied force applied across its entire area, than the regional confidence factor would be equal to 100%, since the relative magnitude would be equal to the total applied force when calculated using the system equations from step 310. This process would be repeated for each sensing region 122A-E within a sensing area 120 so that a regional confidence factor for each sensing region 122A-E is calculated.

Still referring to FIG. 3, at step 314, a raw confidence factor is determined. Referring to the example described in the preceding paragraphs, a raw confidence factor is determined based on the first regional confidence factor and the second regional confidence factor. In some embodiments, the raw confidence factor is determined by averaging the first regional confidence factor and the second regional confidence factor. The raw confidence factor is an average of each of the regional confidence factors in some embodiments. For example, if each of the regional confidence factors from step 312 were equal to 100%, then that would represent that all of the force imparted to a sensing area 120 was captured by the activated sensing regions 122A-E. This would yield a raw confidence factor of 100%, where the equation governing the raw total confidence is as follows: Raw Confidence Factor ($RCF_N$)=(($RCF_1+RCF_2+ \ldots +RCF_N$)/N)*100%.

At step 316, the raw confidence factor is compared to a threshold confidence factor. For example, in some embodiments it is determined if the raw confidence factor is below a threshold confidence factor. If a regional confidence factor were not equal to 100%, representing that a particular sensing region 122A-E did not receive the full force applied across its total area, then the raw confidence factor would be less than 100%, and may dip below an acceptable confidence factor threshold. In embodiments, the threshold confidence factor may be set by a user prior to performing the method, or may be preset to help avoid injury to a user. For example, the threshold confidence factor may be set to a 90% threshold, where the raw confidence factor represents the system's confidence in that is collected all the force applied to the sensing regions 122A-E.

At step 318, a correction algorithm is initiated to calculate a corrected confidence factor. In some embodiments, the determination to perform the correction algorithm is based on a comparison of the raw confidence factor and a threshold confidence factor of step 316. In some embodiments, the correction algorithm to calculate the corrected confidence factor is performed if the raw confidence factor is below the threshold confidence factor. In the event the raw confidence factor falls below the threshold confidence factor, it is determined that a portion of the force applied to a sensing area 120, and particularly to a sensing region 122A-E, was not applied properly to the glove apparatus 100, and instead was applied to the non-inclusive regions 126, 128. This is detrimental in situations where the glove apparatus 100 is being used to monitor the ergonomics of a user performing a task. If the force applied to the sensing area 120 is not applied correctly, this can lead to fatigue problems and injury to the user. In some embodiments, in order to ensure that force applied to the glove is not missed, and to ensure total applied force is measured appropriately, a non-inclusive non-discrete correction algorithm is performed on sensing regions 122A-E where the relative magnitude is not equal to the total applied force, as will be described further below.

Still referring to FIG. 3, at step 320, a non-inclusive region is determined. Referring to the example described in the preceding paragraphs, a portion of the force applied to the sensor system 10 was applied to the non-inclusive region 126 based on the first regional confidence factor of the first sensing region 122A and the second regional confidence factor of the second sensing region 122B. The glove apparatus may be pre-calibrated to expect a certain force applied to the sensing regions 122, which the sensor system 10 has learned through an algorithm with in its software. Over time, as the same motion is performed by a user wearing the glove apparatus 10, such as inserting a bolt, the sensor system 10 learns to expect a certain threshold level of detected force. If this threshold level is not met, then the raw confidence factor will fall below the threshold level, indicating that all the force applied to the sensor system 10 is not detected in the total applied force measurement.

At step 322, an activation area is determined. Referring to the example described in the preceding paragraphs, the determination of the activation area of the non-inclusive region is based on the plurality of activated states of the plurality of sensors of the first sensing region 122A and the second sensing region 122B. As stated above, a sensing area 120 is formed from a plurality of sensing regions 122A-E, which may be identical or different sizes. Based on the loading of each individual sensing region 122A-E within a sensing area 120, the activation area of the sensing area 120 is able to be determined, which corresponds to which sensing regions 122A-E within the sensing area 120 that are not fully loaded across their total area. For example, if the first sensor 124A is fully loaded, but the adjacent second sensing region 122B is not fully loaded, having a low regional confidence factor, it may be determined that a force is being applied to the non-inclusive region 126. This also applies when multiple sensing regions 122A-E are in an activated state and fully loaded, which may show the pressure gradient across the whole sensing area 120 and bordering the non-inclusive region 126.

At step 324, a force distribution is determined. Referring to the example described in the preceding paragraphs, the determination of the force distribution of the non-inclusive region based on the peak generated electrical signals of the plurality of sensors of the first sensing region 122A and the second sensing region 122B. If some of the sensing regions 122A-E are fully loaded on one side of the sensing area 120, but the force readings decrease as the force is applied across the sensing area 120 to the opposite side, such as across the second sensing region 122B and towards the fourth sensing region 122D, this may indicate that a force is applied to the non-inclusive region 126. Since the second sensing region 122B is not fully loaded, this would cause a discrepancy in the relative magnitude of that particular sensing region 122B, and therefore cause a lowering in the raw regional confidence factor. The non-inclusive non-discrete correction algorithm would determine the activation area of the non-inclusive region 126 and the amount of force expected to be applied to the non-inclusive region 126. For example, based on the surrounding sensing regions 122A and 122C-E, the non-inclusive non-discrete correction algorithm would determine that a non-inclusive region 126 only has an activation area and load of 75% of a predetermined total area. As explained above, the sensor system 10 would determine the expected force from performing the assembly action, and would also determine the total area to expect when a force is applied. For example, a bolt would be expected to have the same area every time one is inserted into a component.

At step 326, a corrected corresponding peak force measurement of the non-inclusive region is calculated. Referring to the example described in the preceding paragraphs, the corrected corresponding peak force measurement is based on the activation area and force distribution of the first sensing region 122A and the second sensing region 122B. The corrected corresponding peak force measurement of the non-inclusive region may be a scaled peak force measurement based on a stored calibration curve. Referring to the example described in the preceding paragraphs, after determining which sensing regions 122A-E are activated, and how the force is distributed across the sensing area 120, a corrected corresponding peak force measurement can be calculated for the non-inclusive region 126. The corrected corresponding peak force measurement may be a scaled value of the measured peak force used to calculate the raw confidence factor. In some embodiments, in order to scale the corrected corresponding peak force measurement appropriately, an algorithm developed using artificial intelligence from controlled experiments in a lab setting may be used to determine the scaled corrected corresponding peak force measurement. The artificial intelligence algorithm is based on the activation area and force distribution, and their relationship to the total applied force. Additionally, in some embodiments, stored calibrations for a plurality of measured activation areas and force distributions may be used to scale the corrected corresponding peak force measurement. If an exact match does not exist within the stored calibrations, a scale factor can be interpolated between stored calibrations in order to determine the corrected corresponding peak force measurement.

Still referring to FIG. 3, at step 328, a corrected regional confidence factor for the non-inclusive region is determined. Referring to the example described in the preceding paragraphs, the corrected regional confidence factor may be based on the corresponding peak force measurement for the non-inclusive region, the total applied force, and at least a portion of a total area of the sensing area. For example, using the corrected corresponding peak force measurement from step 326, the system equations for sensing regions 122A, 122B from step 310, and a portion of the total area of the sensing area 120, a corrected regional confidence factor for non-inclusive region 126 can be calculated.

At step 330, a corrected confidence factor is determined. Referring to the example described in the preceding paragraphs, the corrected confidence factor is determined by averaging the regional confidence factors of the first sensing region 122A, the second sensing region 122B, and the corrected regional confidence factor of the non-inclusive region 126. Similar to step 314, the corrected confidence factor is representative of all of the force applied to the sensor system 10.

At step 332, the corrected confidence factor is compared to the threshold confidence factor. The corrected confidence factor may be higher than the raw confidence factor, since the corrected confidence factor includes all force applied to the sensor system 10.

In some embodiments, once the corrected confidence factor is calculated, the corrected confidence factor may be displayed to a user so the user is aware of the confidence factor. If the corrected confidence factor is still below the threshold confidence factor, it may require the user to perform the movement again, with a new data collection process. If the corrected confidence factor is below the threshold value, it may show that a force was applied to an area of the sensor system 10 that did not have a sensing area 120, which may correlate to bad ergonomics of the user.

Figure 4:
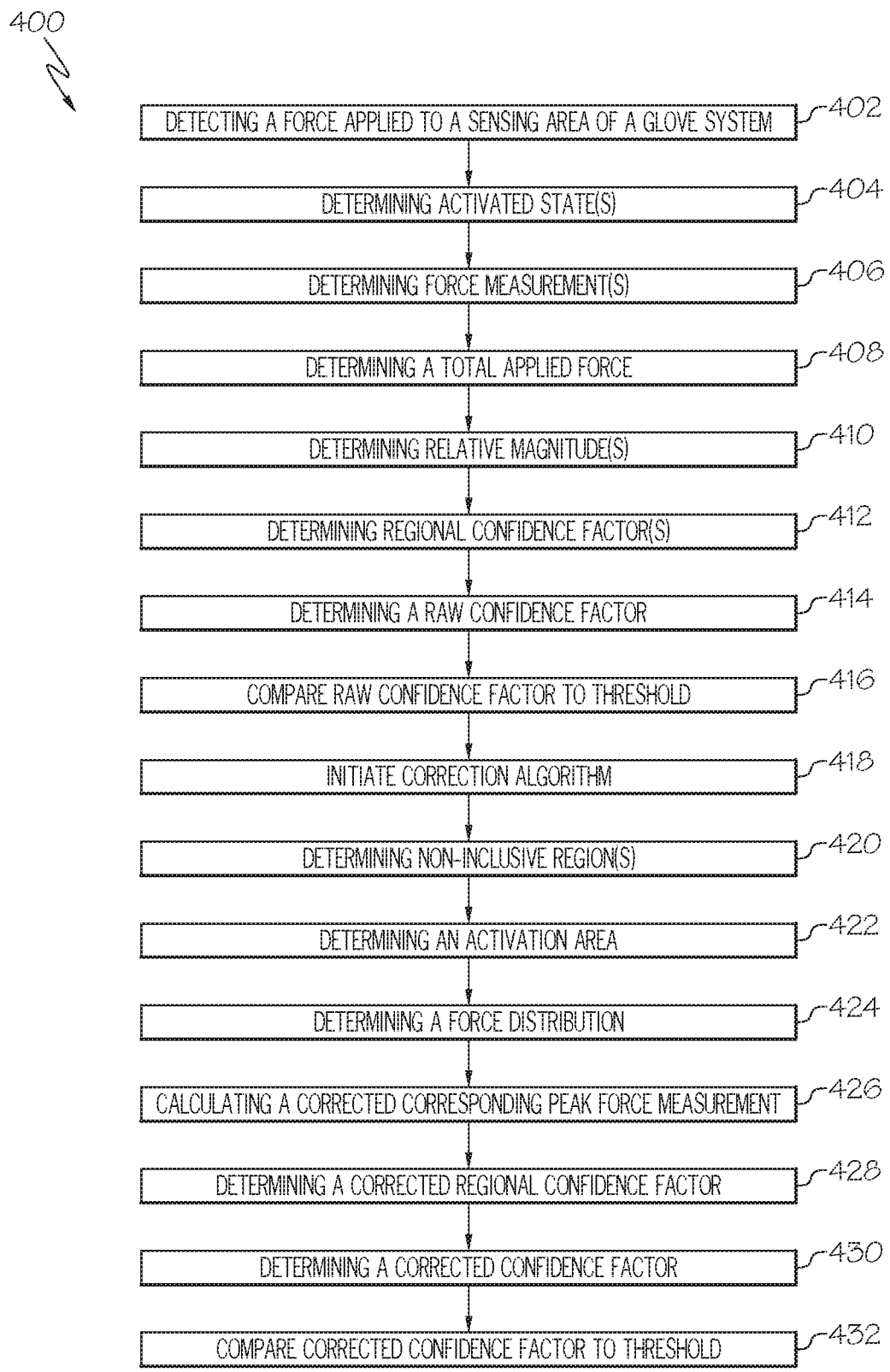
FIG. 4 depicts a flow diagram of an illustrative method of distributing a force across the sensing area and non-inclusive region of the sensing sensor system of FIG. 2B according to one or more embodiments shown and described herein.

Referring now to the flow diagram of FIG. 4 in conjunction with FIGS. 2A and 2B, an illustrative method 400 of localizing and measuring a force load applied to the glove apparatus 200 is schematically depicted. More specifically, the glove apparatus 200 is operable to measure a resultant pressure generated from a force load received along the one or more sensing areas 220 on a surface of an occupant's hand. The depiction of FIG. 4 and the accompanying description below is not meant to limit the subject matter described herein or represent an exact description of how forces may be localized and measured, but instead is meant to provide a simple schematic overview to illustrate the general force localization characteristics of the method described herein.

Referring now to FIG. 4, in conjunction with the sensor system 20 of FIGS. 2A and 2B, a flow diagram is schematically depicted of an illustrative method 400 of determining a pressure magnitude in response to the glove apparatus 200 receiving a force applied thereon. Initially, at step 402, a force applied to a sensing area of a sensor system is detected. Referring to FIG. 2B, the sensing area 220 includes a first sensing region 222A and a second sensing region 222B, the first sensing region 222A including a first plurality of sensors 224A, and the second sensing region 222B including a second plurality of sensors 224B. As stated above, a sensing area 220 may include a plurality of sensing regions 222A-E, with each sensing region 222A-E including a plurality of sensors 224A-E, as depicted in FIG. 2B. The applied force generates an electrical signal within each of the plurality of sensors 224A-E. This allows the sensors 224A-E arranged within the sensing regions 222A-E detect the force applied to the sensing regions 222A-E, respectively. The amount of sensors 224A within the first sensing region 222A can vary depending on the size and shape of the first sensing region 222A. Additionally, the amount of sensors 224B within the second sensing region 222B can vary depending on the size and shape of the second sensing region 222B. In this instance, the force data detected by the sensors 224A-E is transmitted to the server computing device 14 of the sensor system 20 via the computer network 16 in the form of an electrical signal 15. As a user wears the glove apparatus 200 and then performs some task (e.g., pushing a box, inserting a screw), a force is applied to the glove apparatus 200. This input force is received by the sensing areas 220 which are arranged on the surface of the glove apparatus 200.

At step 404, a plurality of activated states of the plurality of sensors of sensing regions is determined. The determination of activated states of the plurality of sensors is based on the detected force of the plurality of sensors. Referring to FIG. 2B, the first sensing region 222A is placed in an inactive state if the detected force of the first sensing region 222A is outside a ratio threshold when compared to the detected force of the second sensing region 222B. As the force is applied to the sensing area 220, an electrical signal is produced by the plurality of sensors 224A-E of the sensing regions 222A-E in response to the force. The electrical signal can be produced through a piezoelectric material, a potentiometer, or the like arranged within the sensing areas 220.

The server computing device 14 determines whether a state of the sensing regions 222A-E receiving the force is in an activated state or an inactivated state. The determination of an activated state is based on the electrical signal of each individual sensor 2224A-E, and comparing the values of each electrical signal. For example, if a single sensing region, such as the fifth sensing region 222E, having the plurality of sensors 224E, produces an electrical signal significantly less that the other sensing regions 222A-D, then it would be determined that the fifth sensing region 222E is in an inactivated state, and may be removed from further calculations, while the sensing regions 222A-222D may be determined to be in an activated state. Accordingly, it should be understood that in some instances the sensing regions 222A-E that receive a force applied thereto may not detect the force along the individual, discrete area of the sensing regions 222A-E.

At step 406, a plurality of force measurements are determined based on electrical signals of the plurality of sensors. For example, first force measurements of the first plurality of sensors 224A may be determined based on a generated electrical signal of the first plurality of sensors 224A. In some embodiments, the first force measurements of the first plurality of sensors 224A are determined based on a peak generated electrical signal of the first plurality of sensors 224A. As a movement is performed by a user, the electrical signal of the first plurality of sensors 224A is recorded (i.e., for a time interval of 5 seconds). After the movement is performed, that electrical signal is compared to a corresponding calibration curve for the first plurality of sensors 224A. The peak force over the time interval experienced by the first plurality of sensors 224A is then determined. Additionally, for example, second force measurements of the second plurality of sensors 224B may be determined based on a generated electrical signal of the second plurality of sensors 224B. In some embodiments, the second force measurements of the second plurality of sensors 224B are determined based on a peak generated electrical signal of the second plurality of sensors 224B. Similar to the how the force measurement of the first sensor 224A is determined, as a movement is performed by a user, the electrical signal of the second plurality of sensors 224B is recorded (i.e., for a time interval of 5 seconds). After the movement is performed, that electrical signals are compared to a corresponding calibration curve for the second plurality of sensors 224B. The peak force over the time interval experienced by the second plurality of sensors 224B is then determined. The peak force measurements are calculated using stored calibration curves including the relationship between the peak generated electrical signals and a corresponding force measurement. During a procedure, a user may push on an object while wearing the sensor system 20. Over the time interval of the procedure, a the force applied is detected at a sampling rate of 20-40 Hz, although other sampling rates may be considered. The peak electrical signal generated by a sensing regions 222A-E may be translated into a peak force value based on a stored calibration curve. The stored calibration curves may be compiled in a lab setting where various known forces were applied to the sensing regions 222, and the corresponding electrical signals were recorded in order to create the stored calibration curve over the effect measuring range of the sensing regions 222A-E. For example, if a voltage of 2 volts is being read in by the first plurality of sensors 224A of the first sensing region 222A, then the corresponding force value when the first plurality of sensors 224A is detecting 2 volts may be 20 lbf applied to the first sensing region 222A.

Still referring to FIG. 4, at step 408, a total applied force is determined. Referring to the example being described in the preceding paragraphs, the total applied force may be determined based on the force measurements. The total applied force is determined by summing the plurality of peak force measurements of the first plurality of sensors 224A and the second plurality of sensors 224B, respectively. After each sensing region 222A-E has its peak force measurements calculated based on the stored calibration curves, each of the peak force measurements are summed together to determine the peak total applied force across the sampling rate. For example, the total applied force is represented by the following equation: $F_{Total} = F_1 + F_2 + \ldots + F_N$, where N is the total number of sensing regions 222A-E within a sensing area 220.

At step 410, relative magnitudes of the sensing regions are determined. Referring to the example described in the preceding paragraphs, a first relative magnitude of the first sensing region 222A is determined based on the force measurements of the plurality of sensors 224A of the first sensing region 222A, a first area of the first sensing region 222A, and at least a portion of the total area of the sensing area 220. In some embodiments, the first relative magnitude of the first sensing region 222A is determined based on the peak force measurements of the plurality of sensors 224A of the first sensing region 222A, the first area of the first sensing region 222A, and at least a portion of the total area of the sensing area 220. Additionally, for example, a second relative magnitude of the second sensing region 222B is determined based on the force measurements of the plurality of sensors 224B of the second sensing region 222B, the first area of the first sensing region 222A, and at least a portion of the total area of the sensing area 220. In some embodiments, the second relative magnitude of the second sensing region 222B is determined based on the peak force measurements of the plurality of sensors 224B of the second sensing region 222B, the first area of the first sensing region 222A, and the second area of the second sensing region 222B. As stated above, a sensing area 220 may be broken into various sensing regions 222A-E of different sizes across which a total force is applied. The relative magnitude ($F_R$) of a sensing region 222A-E is represented by the equation: Relative Magnitude $(F_{RN})$ = (Applied Force $(F_N)$/Area of Sensing Region $(A_N)$). Since the total applied force is applies across the sensing area 220, each of the sensing regions 222A-E may be related to one another based on the area of each sensing region 222A-E and the total applied force to the sensing area 220. For example, if a first sensing region 222A has half as much area as a second sensing region 222B, then the force applied to the second sensing region 222B ($F_2$) in terms of the force applied to the first sensing region 222A ($F_1$) would be half of $F_1$. A system equation for each individual sensing region 222A-E within a sensing area 220 may be created, placing the forces applied to each sensing region 222A-E in terms of that particular sensing region's measured peak applied force. If the sensing regions 222A-E of a sensing area 220 all had the applied force applied across their total area, then each of the system equations for the sensing regions 222A-E would equal the total applied force. If a sensing region 222A-E did not have a force applied across its total area, then the force calculated by the system equation using the relative magnitudes would be less than the total applied force.

At step 412, regional confidence factors for the sensing regions are determined. Referring to the example described in the preceding paragraphs, a first regional confidence factor for the first sensing region 222A is determined based on the first relative magnitude and the total applied force. Additionally, for example, a second regional confidence factor for the second sensing region 222B is determined based on the second relative magnitude and the total applied force. The equation to calculate a regional confidence factor is as follows: Regional Confidence Factor $(RCF_N) = F_{RN}/F_{Total}$. If a sensing region 222A-E had the total applied force applied across its entire area, than the regional confidence factor would be equal to 100%, since the relative magnitude would be equal to the total applied force when calculated using the system equations described above. This process would be repeated for each sensing region 222A-E within a sensing area 220 so that a regional confidence factor for each sensing region 222A-E is calculated.

Still referring to FIG. 4, at step 414, a raw confidence factor is determined. Referring to the example described in the preceding paragraphs, a raw confidence factor is determined based on the first regional confidence factor and the second regional confidence factor. The raw confidence factor is determined by averaging the first regional confidence factor and the second regional confidence factor in some embodiments. The raw confidence factor is an average of each of the regional confidence factors in some embodiments. For example, if each of the regional confidence factors from step 312 where equal to 100%, then that would represent that all of the force imparted to a sensing area 220 was captured by the sensing regions 222A-E. This would yield a raw confidence factor of 100%, where the equation governing the raw total confidence is as follows: Raw Confidence Factor $(RCF_N) = ((RCF_1 + RCF_2 + \ldots + RCF_N)/N)*100\%$.

At step 416, the raw confidence factor is compared to a threshold confidence factor. For example, in some embodiments it is determined if the raw confidence factor is below a threshold confidence factor. If a regional confidence factor were not equal to 100%, representing that a sensing region 222A-E did not receive the full force applied across its total area, then the raw confidence factor would be less than 100%, and may dip below an acceptable confidence factor threshold. In embodiments, the threshold confidence factor may be set by a user prior to performing the method, or may be preset to help avoid injury to a user. For example, the threshold confidence factor may be set to a 90% threshold, where the raw confidence factor represents the system's confidence in that is collected all the force applied to the sensing regions 222A-E.

At step 418, a correction algorithm is initiated to calculate a corrected confidence factor. In some embodiments, the determination to perform the correction algorithm is based on a comparison of the raw confidence factor and a threshold confidence factor of step 416. In some embodiments, the correction algorithm to calculate the corrected confidence factor is performed if the raw confidence factor is below the threshold confidence factor. In the event the raw confidence factor falls below the threshold confidence factor, it is determined that a portion of the force applied to a sensing area 220, and particularly to a sensing region 222A-E was not applied properly to the glove apparatus 200, and instead was applied to the non-inclusive regions 226, 228. This is detrimental in situations where the glove apparatus 200 is being used to monitor the ergonomics of a user performing a task. If the force applied to the sensing area 220 is not applied correctly, this can lead to fatigue problems and injury to the user. In some embodiments, in order to ensure that force applied to the glove is not missed, and to ensure total applied force is measured appropriately, a non-inclusive discrete correction algorithm is performed on sensing regions 222A-E which a relative magnitude not equal to the total applied force, as will be described further below.

Still referring to FIG. 4, at step 420, a non-inclusive region is determined. Referring to the example described in the preceding paragraphs, a portion of the force applied to the sensor system 20 was applied to the non-inclusive region 226 based on the first regional confidence factor of the first sensing region 222A and the second regional confidence factor of the second sensing region 222B. The glove apparatus may be pre-calibrated to expect a certain force applied to the sensing regions 222, which the sensor system 20 has learned through an algorithm with in its software. Over time, as the same motion is performed by a user wearing the sensor system 20, such as inserting a bolt, the sensor system 20 learns to expect a certain threshold level of detected force. If this threshold level is not met, then the raw confidence factor will fall below the threshold level, indicating that all the force applied to the sensor system 20 is not detected in the total applied force measurement.

At step 422, an activation area is determined. Referring to the example described in the preceding paragraphs, the determination of the activation area of the non-inclusive region is based on the plurality of activated states of the plurality of sensors of the first sensing region and the second sensing region. As stated above, a sensing area 220 is formed from a plurality of sensing regions 222A-E, with each sensing regions 222A-E having a plurality of sensors 224A-E arranged therein, respectively. The sensing regions 222A-E may be identical or different sizes, and may have different amounts of sensors 224A-E. Based on the loading of each individual sensor 224A-E within a sensing region 222A-E, which is within a sensing area 220, the activation area of the sensing area 220 is able to be determined, which corresponds to which sensing regions 222A-E within the sensing area 220 are not fully loaded across their total area. For example, if the first plurality of sensors 224A is fully loaded, but the adjacent second plurality of sensors 224B are not fully loaded, having a low regional confidence factor, it may be determined that a force is being applied to the non-inclusive region 226. This also applies when multiple sensing regions 222A-E are in an activated state and fully loaded, which may show the pressure gradient across the whole sensing area 120 and bordering the non-inclusive region 226.

At step 424, a force distribution is determined. Referring to the example described in the preceding paragraphs, the determination of the force distribution of the non-inclusive region is based on the applied force to each sensor of the plurality of sensors of the first sensing region and the second sensing region. If some of the sensors 224B within the second sensing region 222B are fully loaded on one side of the second sensing region 222B, but the force readings decrease as the force is applied across the second sensing region 222B to the opposite side, such as across the second sensing region 222B and towards the fourth sensing region 222D, this may indicate that a force is applied to the non-inclusive region 226. Since the second sensing region 222B is not fully loaded, this would cause a discrepancy in the relative magnitude of the second sensing region 222B, and therefore cause a lowering in the raw regional confidence factor. The non-inclusive discrete correction algorithm would determine the activation area of the non-inclusive region 226 and the amount of force expected to be applied to the non-inclusive region 226. For example, based on the surrounding sensing regions 222A and 222C-E, the non-inclusive discrete correction algorithm would determine that a non-inclusive region 226 only has an activation area and load of 75% of a predetermined total area. As explained above, the sensor system 20 would determine the expected force from performing the assembly action, and would also determine the total area to expect when a force is applied. For example, a bolt would be expected to have the same area every time one is inserted into a component.

At step 426, a corrected corresponding peak force measurement of the non-inclusive region is calculated. Referring to the example described in the preceding paragraphs, the corrected corresponding peak force measurement is based on the activation area and force distribution of the first sensing region and the second sensing region. The corrected corresponding peak force measurement of the non-inclusive region is determined based on the activation area and force distribution of the non-inclusive region 226 may be a scaled peak force measurement based on a stored calibration curve. After determining which sensors 224A-E within the sensing regions 222A-E are activated, and how the force is distributed across the sensing regions 222A-E, a corrected corresponding peak force measurement can be calculated for the non-inclusive region 226. The corrected corresponding peak force measurement may be a scaled value of the measured peak force used to calculate the raw confidence factor. In some embodiments, in order to scale the corrected corresponding peak force measurement appropriately, an algorithm developed using artificial intelligence from controlled experiments in a lab setting may be used to determine the scaled corrected corresponding peak force measurement. The artificial intelligence algorithm is based on the activation area and force distribution, and their relationship to the total applied force. Additionally, in some embodiments, stored calibrations for a plurality of measured activation areas and force distributions may be used to scale the corrected corresponding peak force measurement. If an exact match does not exist within the stored calibrations, a scale factor can be interpolated between stored calibrations in order to determine the corrected corresponding peak force measurement.

Still referring to FIG. 4, at step 428, a corrected regional confidence factor for the non-inclusive region is determined. Referring to the example described in the preceding paragraphs, the corrected regional confidence factor may be based on the corresponding peak force measurement for the non-inclusive region, the total applied force, and at least a portion of a total area of the sensing area. Using the corrected corresponding peak force measurement from step 426, and the system equations for the first sensing region 222A and the second sensing region 222B from step 420, a corrected regional confidence factor for the non-inclusive region 126 can be calculated.

At step 430, a corrected confidence factor is determined. Referring to the example described in the preceding paragraphs, the corrected confidence factor is determined by averaging the regional confidence factors of the first sensing region 222A, the second sensing region 222B, and the corrected regional confidence factor of the non-inclusive region 226. Similar to step 414, the corrected confidence factor is representative of all of the force applied to the sensor system 20.

At step 432, the corrected confidence factor is compared to the threshold confidence factor. The corrected confidence factor may be higher than the raw confidence factor, since the corrected confidence factor includes force applied to the sensor system 20.

Figure 5:
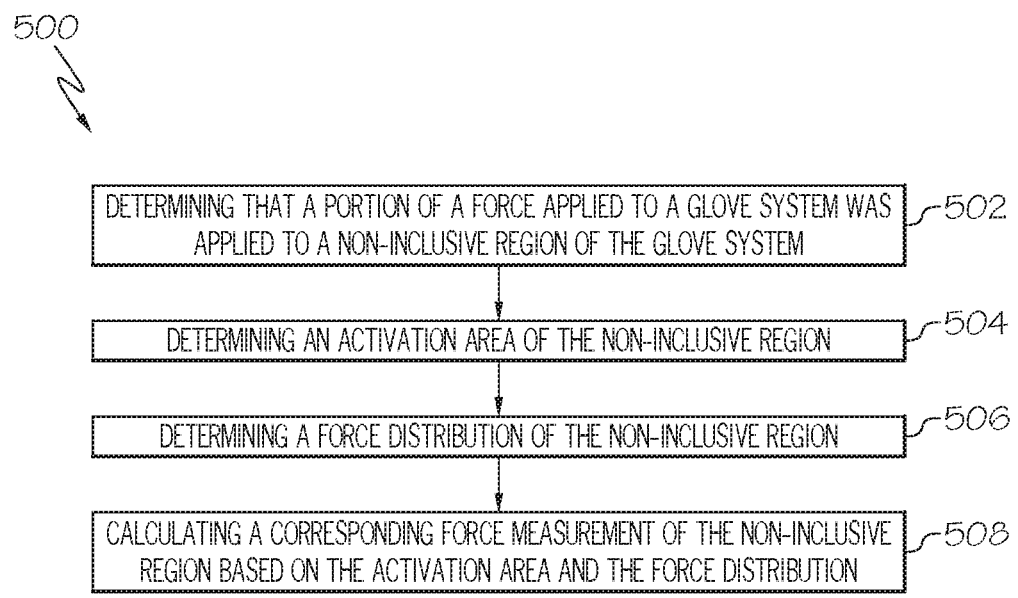
FIG. 5 depicts a flow diagram of an illustrative method of distributing a force across the sensing area and non-inclusive region of the sensing sensor system of FIG. 1B according to one or more embodiments shown and described herein.

Referring now to the flow diagram of FIG. 5 in conjunction with FIGS. 1A-2B, an illustrative method 500 of determining a force load applied to a non-inclusive region 126 of the glove apparatus 100 is schematically depicted. More specifically, the glove apparatus 100 is operable to measure a resultant pressure generated from a force load received along the one or more sensing areas 120 on a surface of an occupant's hand. The depiction of FIG. 5 and the accompanying description below is not meant to limit the subject matter described herein or represent an exact description of how forces may be localized and measured, but instead is meant to provide a simple schematic overview to illustrate the general force localization characteristics of the method described herein.

Referring now to FIG. 5, in conjunction with the sensor system 10 of FIGS. 1A and 1B, a flow diagram is schematically depicted of an illustrative method 500 of determining a pressure magnitude applied to a non-inclusive region 126 of the glove apparatus 100 receiving a force applied thereon. Initially, at step 502, it is determined that a portion of a force applied to a sensor system was applied to a non-inclusive region of the sensor system. Referring to the example described in the preceding paragraphs, as a user is performing an assembly operation, the user will apply a force to an object, such as a bolt, in order to insert the object. If the user does not apply the force completely across a sensing area 122A-E, then a portion of the force will be applied to the non-inclusive region 126, where no sensors are arranged. This determination is made since the sensor system 10 may be expecting a certain threshold level of applied force, either through a threshold range created from machine learning algorithm after many processes are performed with the sensor system 10, or if the range is a preset range.

At step 504, an activation area of the non-inclusive region is determined. Referring to the example described in the preceding paragraphs, the activation area of the non-inclusive region 126 is determined based on the plurality of activated states of the sensors 124A, 124B of the first sensing region 122A and the second sensing region 122B. Additionally, the activation area of the non-inclusive region 126 is based on a stored profile geometry from a plurality of activation areas, such as bolts or panels which are pressed upon during an assembly process.

At step 506, a force distribution of the non-inclusive region is determined. Referring to the example described in the preceding paragraphs, the force distribution of the non-inclusive region 126 is based on the plurality of activated states of the sensors 124A, 124B of the first sensing region 122A and the second sensing region 122B and a predicted applied force to the sensor system 10. As the sensor system 10 is used, the sensor system 10 may learn how much force is to be expected for an assembly process. For example, if a user is performing the same operation while wearing the sensor system 10, the system will be able to determine an acceptable range of force applied to the sensor system. Based on this the sensor system will be able to determine what portion of the force was applied to the sensing regions 122A-E, and which portion was applied to the non-inclusive region 126.

At step 508, a corresponding force measurement of the non-inclusive region based on the activation area and the force distribution is determined. Referring to the example described in the preceding paragraphs, based on the activation area and the force distribution, the non-inclusive region 126 may be quantified virtually so that the sensor system 10 may determine how much force was applied to the sensor system 10 as a whole. This corresponding force measurement may then be used in the total applied force equation in combination with the relative magnitudes of the other sensing regions 122A-E which also had a force applied to them.

In embodiments, once the corrected confidence factor is calculated, the corrected confidence factor may be displayed to a user so the user is aware of the confidence factor. If the corrected confidence factor is still below the threshold confidence factor, it may require the user to perform the movement again, with a new data collection process. If the corrected confidence factor is below the threshold value, it may show that a force was applied to an area of the sensor system 20 that did not have a sensing area 220, which may correlate to bad ergonomics of the user.

Accordingly, the embodiments describe herein improve an accuracy of measuring a pressure received along a sensor assembly of the glove by determining an actual active area of a sensor that receives a force thereon for incorporation into actual force computations. Providing a sensor system that localizes an inclusive force received along a sensor may assist in accurately measuring a resultant pressure calculated from a force applied thereto. The sensor system may aid in determining an appropriate method, such as a physical position or orientation, in performing a task by detecting and measuring various forces received at an operator's hand at an actual active area along a surface of the operator's hand with accuracy by localizing the area that the force was received on the sensor system for accurate measurement.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method comprising:
    detecting a force applied to at least a portion of a sensing area of a sensor system, the sensing area including a first sensing region and a second sensing region, each of the first sensing region and the second sensing region including a sensor, a non-inclusive region adjacent the sensing area;
    determining a first force measurement of the first sensing region based on a generated electrical signal of the sensor of the first sensing region;
    determining a second force measurement of the second sensing region based on a generated electrical signal of the sensor of the second sensing region;
    determining a total applied force based on the first force measurement and the second force measurement;
    determining a first relative magnitude of the first sensing region based on the first force measurement of the sensor of the first sensing region, an area of the first sensing region, and at least a portion of a total area of the sensing area;
    determining a second relative magnitude of the second sensing region based on the second force measurement of the sensor of the second sensing region, an area of the second sensing region, and at least the portion of the total area of the sensing area;
    determining a first regional confidence factor for the first sensing region based on the first relative magnitude and the total applied force;
    determining a second regional confidence factor for the second sensing region based on the second relative magnitude and the total applied force;
    determining a raw confidence factor based on the first regional confidence factor and the second regional confidence factor; and
    initiating a correction algorithm to calculate a corrected confidence factor based on a comparison of the raw confidence factor and a threshold confidence factor, initiating the correction algorithm including:
        determining an activation area of the non-inclusive region;
        determining a force distribution of the non-inclusive region; and
        calculating a corresponding force measurement of the non-inclusive region based on the activation area and the force distribution.

2. The method of claim 1, wherein
each of the first sensing region and the second sensing region including a plurality of sensors.

3. The method of claim 2, wherein:
the first and second force measurements of the plurality of sensors of the first sensing region and of the second sensing region are determined based on peak generated electrical signals of the plurality of sensors of the first sensing region and the second sensing region;
the total applied force is determined by summing a first peak force measurement of the first force measurement and a second peak force measurement of the second force measurement;
the first relative magnitude of the first sensing region is determined based on the first peak force measurement of the plurality of sensors of the first sensing region, the first area of the first sensing region, and at least the portion of the total area of the sensing area;
the second relative magnitude of the second sensing region is determined based on the second peak force measurement of the plurality of sensors of the second sensing region, the first area of the first sensing region, and at least the portion of the total area of the sensing area;
the raw confidence factor is determined by averaging the first regional confidence factor and the second regional confidence factor; and
the correction algorithm to calculate the corrected confidence factor is performed if the raw confidence factor is below the threshold confidence factor.

4. The method of claim 2, wherein the first and second force measurements are calculated using stored calibration curves including the relationship between the peak generated electrical signals and a corresponding force measurement.

5. The method of claim 2, wherein a plurality of activated states of the plurality of sensors of the first sensing region and the second sensing region are based on the detected force.

6. The method of claim 5, wherein the activation area of the non-inclusive region is based on a stored profile geometry from a plurality of activation areas.

7. The method of claim 6, wherein the activation area of the non-inclusive region is determined based on the plurality of activated states of the plurality of sensors of the first sensing region and the second sensing region.

8. The method of claim 7, wherein the force distribution of the non-inclusive region is based on the plurality of activated states of the plurality of sensors of the first sensing region and the second sensing region and a predicted applied force to the sensor system.

9. The method of claim 1, wherein:
the first and second force measurements of the sensors of the first sensing region and of the second sensing region are determined based on peak generated electrical signals of the sensors of the first sensing region and the second sensing region;
the total applied force is determined by summing a first peak force measurement of the first force measurement and a second peak force measurement of the second force measurement;
the first relative magnitude of the first sensing region is determined based on the first peak force measurement of the sensor of the first sensing region, the area of the first sensing region, and at least the portion of the total area of the sensing area;
the second relative magnitude of the second sensing region is determined based on the second peak force measurement of the sensor of the second sensing region, the area of the second sensing region, and at least the portion of the total area of the sensing area;
the raw confidence factor is determined by averaging the first regional confidence factor and the second regional confidence factor; and
the correction algorithm to calculate the corrected confidence factor is performed if the raw confidence factor is below the threshold confidence factor.

10. The method of claim 1, wherein the first and second force measurements are calculated using stored calibration curves including the relationship between the peak generated electrical signals and a corresponding force measurement.

11. The method of claim 1, wherein a plurality of activated states of the sensors of the first sensing region and the second sensing region are based on the detected force.

12. The method of claim 11, wherein the activation area of the non-inclusive region is based on a stored profile geometry from a plurality of activation areas.

13. The method of claim 12, wherein the activation area of the non-inclusive region is determined based on the plurality of activated states of the sensor of the first sensing region and the second sensing region.

14. The method of claim 13, wherein the force distribution of the non-inclusive region is based on the plurality of activated states of the sensor of the first sensing region and the second sensing region and a predicted applied force to the sensor system.

15. A sensor system comprising:
a sensing area disposed along a surface of the sensor system;
a non-inclusive region arranged adjacent to the sensing area, wherein the non-inclusive region does not include a sensor;
a first sensing region disposed within the sensing area comprising a first sensor configured to detect the force applied to the surface of the sensing area;
a second sensing region disposed within the sensing area comprising a second sensor configured to detect the force applied to the surface of the sensing area; and
a processor that, when executing computer readable and executable instructions of the sensor system, causes the sensor system to:
 detect the force applied to at least a portion of the sensing area of the sensor system, wherein the force creates a plurality of electrical signals within the first sensor and the second sensor;
 determine a first force measurement of the first sensor based on a generated electrical signal of the first sensor;
 determine a second force measurement of the second sensor based on a generated electrical signal of the second sensor;
 determine a total applied force based on the first force measurement and the second force measurement;
 determine a first relative magnitude of the first sensing region based on the first force measurement, an area of the first sensing region, and at least a portion of a total area of the sensing area;
 determine a second relative magnitude of the second sensing region based on the second force measurement, an area of the second sensing region, and at least the portion of the total area of the sensing area;
 determine a first regional confidence factor for the first sensing region based on the first relative magnitude, and the total applied force;
 determine a second regional confidence factor for the second sensing region based on the second relative magnitude, and the total applied force;
 determine a raw confidence factor based on the first regional confidence factor and the second regional confidence factor; and
 initiate a correction algorithm to calculate a corrected confidence factor based on a comparison of the raw confidence factor and a threshold confidence factor, initiating the correction algorithm including:
  determining an activation area of the non-inclusive region;
  determining a force distribution of the non-inclusive region; and
  calculating a corresponding force measurement of the non-inclusive region based on the activation area and the force distribution.

16. The sensor system of claim 15, wherein the first and second force measurements are calculated using stored calibration curves including the relationship between the peak generated electrical signals and a corresponding force measurement.

17. The sensor system of claim 16, wherein a plurality of activated states of the sensors of the first sensing region and the second sensing region are based on the detected force.

18. The sensor system of claim 17, wherein the activation area of the non-inclusive region is based on a stored profile geometry from a plurality of activation areas and on the plurality of activated states of the sensor of the first sensing region and the second sensing region.

* * * * *